US008858061B2

(12) United States Patent
Berman

(10) Patent No.: US 8,858,061 B2
(45) Date of Patent: Oct. 14, 2014

(54) CONCRETE SLUMP MEASUREMENT AND CONTROL SYSTEM

(75) Inventor: Berthold Berman, St. Lasare (CA)

(73) Assignee: Dully Katzeff-Berman, Saint Lazare, QC (CA)

( * ) Notice: Subject to any disclaimer, the term of this patent is extended or adjusted under 35 U.S.C. 154(b) by 951 days.

(21) Appl. No.: 12/993,844

(22) PCT Filed: May 28, 2008

(86) PCT No.: PCT/IB2008/001342
§ 371 (c)(1), (2), (4) Date: Nov. 21, 2010

(87) PCT Pub. No.: WO2009/144523
PCT Pub. Date: Dec. 3, 2009

(65) Prior Publication Data

US 2011/0077778 A1 Mar. 31, 2011

(51) Int. Cl.
*B28C 7/02* (2006.01)
*G01N 33/38* (2006.01)
*G01N 11/00* (2006.01)

(52) U.S. Cl.
CPC ................ *B28C 7/02* (2013.01); *G01N 33/383* (2013.01); *G01N 2011/0046* (2013.01)
USPC ................ 366/10; 366/12; 366/17; 366/142; 366/152.3

(58) Field of Classification Search
CPC . B28C 7/02; G01N 2011/0046; G01N 33/383
USPC ................ 366/10, 12, 13, 16, 17, 142, 152.3
See application file for complete search history.

(56) References Cited

U.S. PATENT DOCUMENTS

| | | | | |
|---|---|---|---|---|
| 1,730,893 | A * | 10/1929 | Lichtenberg | 366/8 |
| 4,318,177 | A * | 3/1982 | Rapp et al. | 700/265 |
| 5,713,663 | A * | 2/1998 | Zandberg et al. | 366/8 |
| 5,752,768 | A * | 5/1998 | Assh | 366/3 |
| 5,948,970 | A * | 9/1999 | Te'eni | 73/54.03 |
| 6,227,039 | B1 | 5/2001 | Te'eni | |
| 6,484,079 | B2 * | 11/2002 | Buckelew et al. | 701/31.4 |
| 6,615,656 | B1 | 9/2003 | Breed et al. | |
| 7,766,537 | B2 * | 8/2010 | Gembala | 366/10 |
| 8,311,678 | B2 * | 11/2012 | Koehler et al. | 700/265 |
| 2008/0103662 | A1 * | 5/2008 | Pillar et al. | 701/50 |
| 2009/0171595 | A1 * | 7/2009 | Bonilla Benegas | 702/41 |

FOREIGN PATENT DOCUMENTS

| | | |
|---|---|---|
| DE | 19952462 | 10/1999 |
| EP | 0308966 | 9/1988 |
| EP | 0924040 | 12/1997 |
| EP | 1961538 | 8/2008 |
| ES | 2281267 | 9/2007 |
| WO | 2007060272 | 5/2007 |

OTHER PUBLICATIONS

PCT/IB08/01342 Notification of Transmittal of International Preliminary Report on Patentability, Dec. 14, 2010.

* cited by examiner

*Primary Examiner* — Tony G Soohoo
(74) *Attorney, Agent, or Firm* — James Ray & Assoc. LLC

(57) ABSTRACT

An apparatus and method to measure and control the slump of concrete by monitoring sensor within the interior surface of a concrete mixer and a liquid flow meter. Data is analyzed by a computer processing unit to determine the slump of the concrete, liquid needed the quantity of concrete within the mixer, the amount of concrete poured, and the starting and ending time of the pour.

16 Claims, 4 Drawing Sheets

LIQUID SUPPLY 14
INPUT MEANS 13
DATA STORAGE 17
VALVE 16
COMPUTER PROCESSING UNIT 12
MIXER 10
FLOW METER 15
FORCE SENSORS 11
MOISTURE SENSOR 20
SENSOR DATA DISPLAY 22
TEMPERATURE SENSOR 21
GPS RECEIVER 30
TRANSMITTER 40
DISPLAY MEANS 18
OUTPUT MEANS 19

Mix Characteristics
Required slump
Mixer characteristics
Calc the required pressure/stress
Measure pressure/stress
Required stress > measured stress
True
False
End
Calc the required quantities of liquids to add
Add the required quantities of liquids (actually the addition will be 85% to 95% of that quantity)

CONCRETE SLUMP MEASUREMENT AND CONTROL SYSTEM

FIELD OF THE INVENTION

The present invention relates, in general, to concrete mixing and, more particularly, this invention relates to measurement and control of slump and to the measurement of the mix.

BACKGROUND OF THE INVENTION

Prior to the conception and development of the present invention, as is generally well known in the prior art, control of mixed concrete slump and pour are critical in providing the desired concrete for particular applications. Slump is a measure of the plasticity of fresh concrete relative to the amount it falls when a slump cone filled with concrete is lifted vertically. The industry testing standards are for example found in ASTM C143. Slump is generally increases with water content of the concrete. Concrete strength is inversely related to the water content in laboratory conditions. However, field conditions make control of the concrete variable more difficult, thus the necessity of obtaining the control of the slump is more critical.

It is known that sensors can be used in the mixing of concrete. For example U.S. Pat. No. 6,484,079 issued to Buckelew et al provides a global positioning satellite receiver to monitor the location of mixers. Similarly, U.S. Pat. No. 5,752,768 issued to Assh and U.S. Pat. No. 5,713,663 issued to Zandberg et al provides a system for control of mixing concrete using sensors. However, these inventions control the mixing using the rotation of the mixing drum in '768 and the torque on the mixer as it rotates in '663. This approach does not produce as good an approximation of the desired slump and does not provide the necessary information to estimate the amount of concrete in the mixer or the start and finish times of the pour.

SUMMARY OF THE INVENTION

The present invention provides an apparatus and method to control the mixing and slump control by use of sensors that by measuring the force applied on the sensor by the concrete either as pressure or stress at the inner surface of the mixer. The applicant has found that the pressure or stress on the sensors is directly related to the slump value. Thus by monitoring the forces on the sensors the desired concrete mix slump can be obtained. The required additional liquid or solids can be added to match the forces on the sensor and therefore the desired slump.

In the conventional mixing process, the mixer is required to idle and count the mixer revolutions to attempt to achieve a consistent mix. The present invention by the monitoring of the force sensors allows the user to charge the mixer and leave the yard by monitoring the maximum forces on the sensor over several revolutions to assure consistency. Similarly where material is added to the mixer, the consistent sensor readings within a generally narrow range allow the user to have improved more direct information that the mix is consistent.

Additionally, the sensors record the loading on the sensors when submerged in the mix and the unloaded sensors emerging from the mix. By measuring the time interval of the submerged sensor and the unloaded sensor as the mixer rotates the user can know the level of the mix within the mixer drum and amount of concrete in the mixer.

Further, the change in the mix level and the start and stop time of the change in level is recorded. Thus the user of the present invention will amount of concrete poured and when it was poured, thus preventing loss through unauthorized pours and an alert as to the need to recharge the mixer.

OBJECTS OF THE INVENTION

It is, therefore, one of the primary objects of the present invention to provide an improved apparatus and method to control concrete mixing.

Another object of the present invention is to provide an improved apparatus to monitor amount of concrete in the mixer.

Another object of the present invention is to provide an improved apparatus to monitor amount of concrete poured.

Still another object of the present invention is to provide an improved apparatus to record the consistency of the concrete mixed during preparation and pour.

Yet another object of the present invention is to provide an apparatus and method to record the time of beginning the pour of mixed concrete and its conclusion.

In addition to the various objects and advantages of the present invention described with some degree of specificity above it should be obvious that additional objects and advantages of the present invention will become more readily apparent to those persons who are skilled in the relevant art from the following more detailed description of the invention, particularly, when such description is taken in conjunction with the attached drawing figures and with the appended claims.

BRIEF DESCRIPTION OF THE BEST MODE

Figure 1:
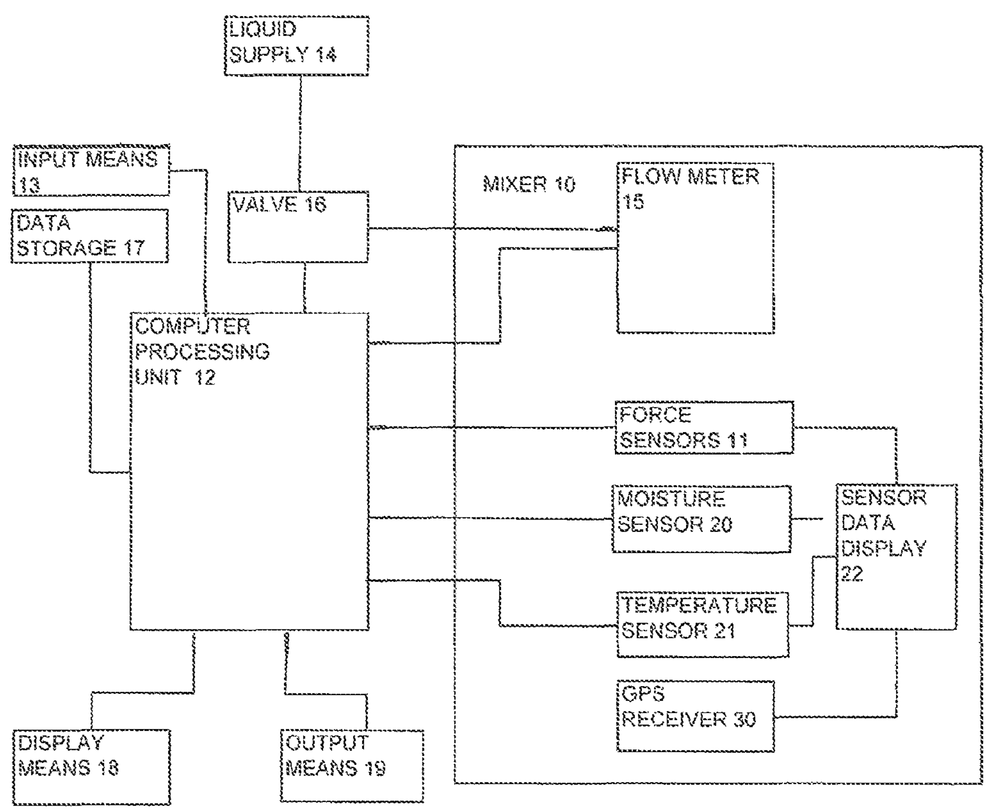
FIG. 1 is a diagram of the apparatus.

Prior to proceeding to the more detailed description of the present invention it should be noted that, for the sake of clarity and understanding, identical components which have identical functions have been identified with identical reference numerals throughout the several views illustrated in the drawing figures.

Figure 2:
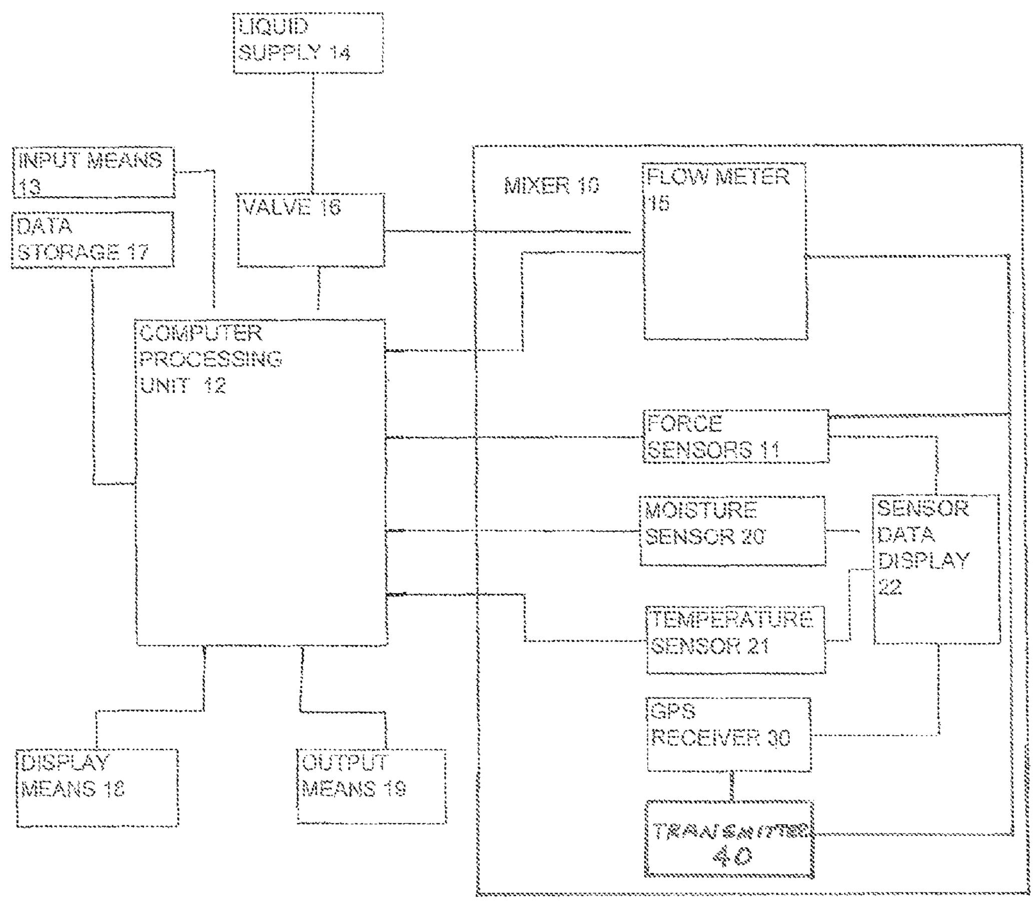
FIG. 2 is a diagram of the apparatus in a second embodiment.

Reference is now made, more particularly, to FIGS. 1 and 2 a concrete mixer 10 has at least one and preferably a plurality of sensors 11 attached to the interior of the mixer 10. The sensors 11 are operably connected to a computer processing unit 12. Particulate matter as an ingredient of concrete is added to the mixer 10. The mixer 10 rotates and the sensors 11 are submerged in the mixer contents and then emerge from the mixture.

The computer processing unit 12 is operably connected to an input means 13, preferably one of a touch screen, voice recognition, keyboard and alphanumeric keypad (not shown). The input means permits the user to enter one or more of the requested slump, mix and customer information.

The desired slump, mix and the customer information is entered by the user. The computer processing unit 12 determines the quantity of liquid to be added to the mixer 10.

The mixer 10 has a liquid supply and line 14 that has a liquid flow meter 15 and a valve 16. The liquid flow meter 15 and valve 16 are operably connected to the computer processing unit 12.

It has been found by the inventor that there is a direct relationship between the pressure or stress on the sensors 12 and the slump. Therefore the slump can be controlled through the analysis of the sensors 12 data.

The computer processing unit 12 also analyzes the data from the sensors 11 to determine the amount of concrete within the mixer by measuring the time difference between the loaded sensor 11 as mixer 10 rotates and the sensors 11 move into the mixture and the unloaded sensors as the sensors 11 emerge from the mixture. The time interval of the unloaded sensors 11 as compared to the loaded sensors 11 indicates the level of the mixture within the mixer 11. As the mixture is poured, the mixture level decreases within the mixer drum. The data from the sensors 11 allows the recording of the change in level of the mixture and time that the level changes. The change in the quantity is the amount poured and the start and end time of the pour is recorded.

The knowledge of the remaining amount and slump of concrete in the mixture allows an adjustment in the quantities of solids and liquid to refill the mixer 10 by the user. The knowledge of the amount poured permits accurate billing of the customer. The start and finish time allow the user to deter unauthorized pours by the mixer operator.

Further, the data is stored in a data storage unit 17 operably connected to the computer processing unit 12 to allow the use of the data as received or for the later retrieval of data.

A display means 18 preferably a computer monitor is operably connected to a computer processing unit 12. Also, an output means 19, preferably one of a printer, is operably connected to the computer processing unit.

Additionally, the preferred embodiment has a moisture sensor 20 and temperature sensor 21 within the mixer 10. This allows the user to further control the concrete. The moisture sensor 20 and temperature sensor 21 are operably connected to the computer processing unit 19.

In the preferred embodiment, the apparatus has a global positioning satellite receiver 30 with a digital output and a transmitter 30. The transmitter 40 is operably connected to the global positioning satellite receiver 30, flow meter 13 and sensors 11 to transmit the location, stress or pressure data and flow of liquid to a remote location. The input means 13, output means 19, computer processing unit 12, data storage unit 17, display means 18 and out put means may separately or in combination be situated at a remote location from the mixer 10.

The sensors 12, moisture sensor 20 and temperature sensor 21 alone or in combination are operably connected to a sensor display 22 that is at the pour location.

The input means can be used by the user to override the computer processing unit 12 and said sensors 11 to manually control the process.

Another embodiment is to use the sensor 11 data as reported on display 22 to control the valve 16 manually.

Figure 3:
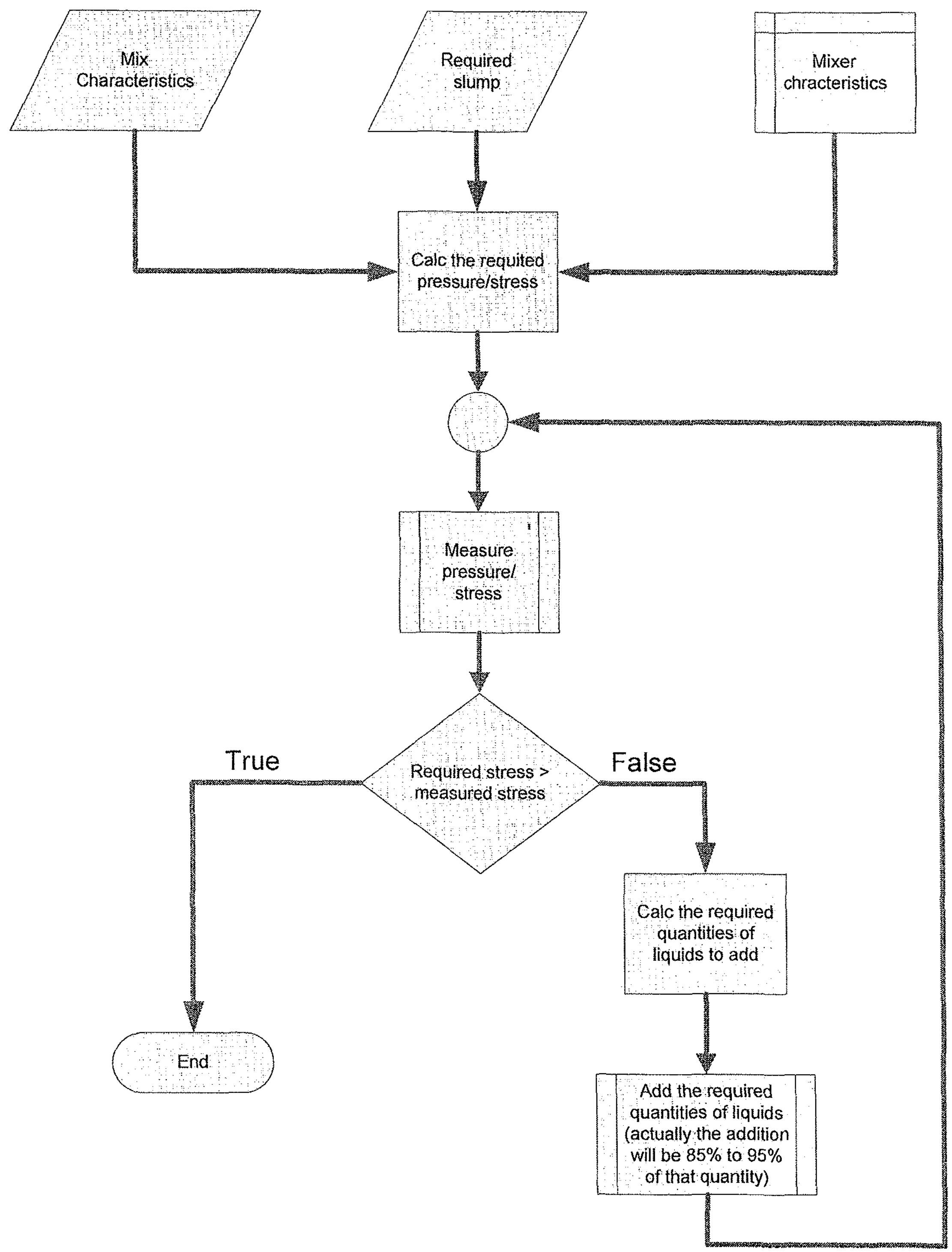
FIG. 3 is a flow chart of the method of controlling slump.
Figure 4:
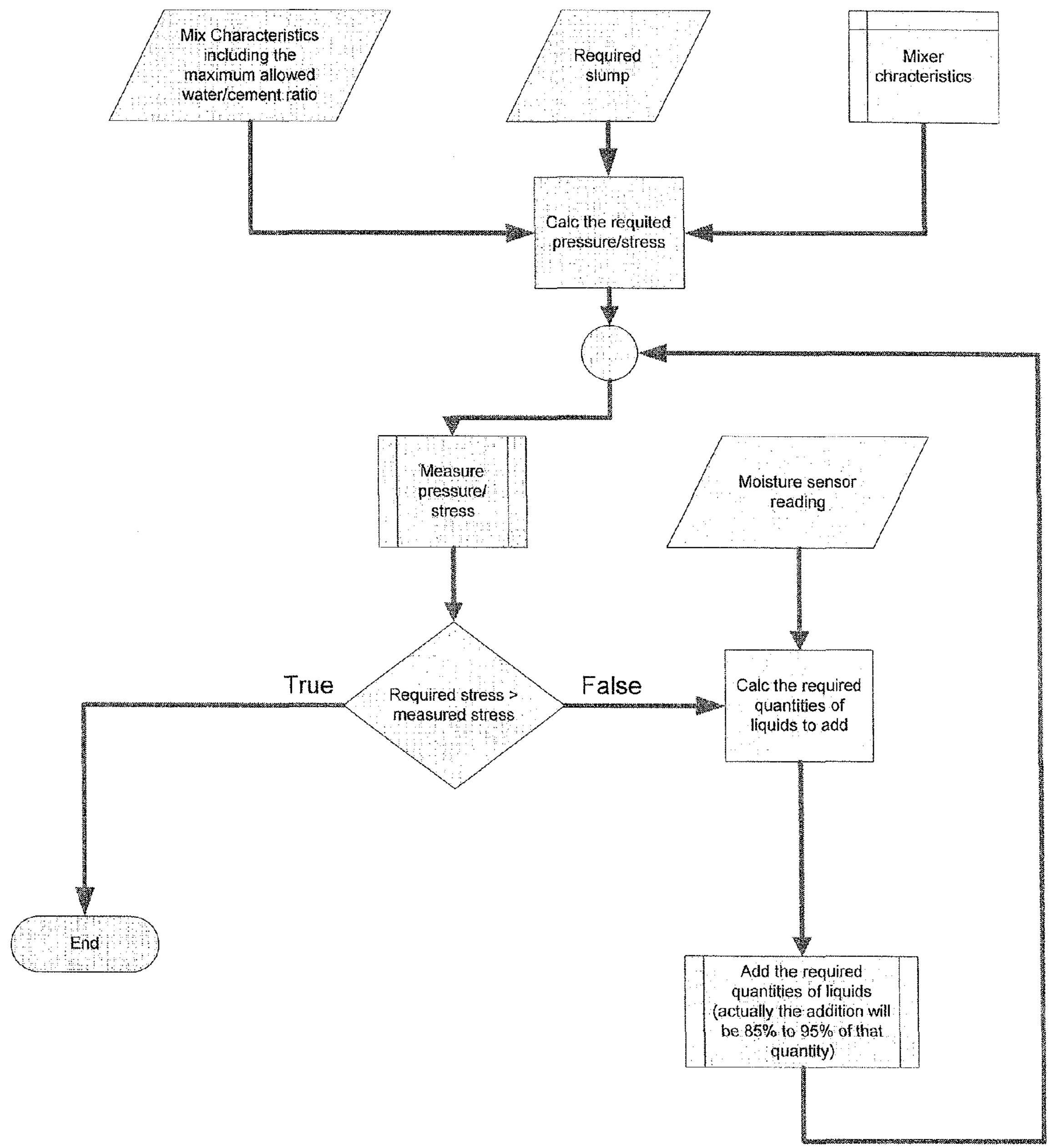
FIG. 4 is a flow chart of the method of controlling slump including a moisture sensor.

Referring FIGS. 3 and 4, the method of controlling the slump, includes the step of entering the slump mix characteristics, including the maximum water to cement ratio, the requested slump and the mixer characteristics. The force on a sensor within a mixer is calculated in terms of pressure or stress. The sensor output is monitored and the amount if any of additional liquid to be added to the mix is calculated. Approximately 85% to 95% of the amount of liquid is added to the mix. The mixer can then leave the plant and any additional liquid can be added at the site of the pour. The stress sensors are monitored and if the force is generally the calculated value the method in complete.

FIG. 4 illustrates the method with the addition of a moisture sensor. As shown in FIG. 4 the additional step is to monitor the moisture monitor and to use this data in calculating any additional liquid.

Also, there is a method to maintain the consistency of the mixture. Rather than count mixer rotations, the present invention includes a method to maintain the consistency by monitoring the sensor and comparing the sensor output over several rotations. The mixture is consistency is acceptable where the sensor data varies less than a predetermined range that varies by concrete application.

While a presently preferred and various alternative embodiments of the present invention have been described in sufficient detail above to enable a person skilled in the relevant art to make and use the same it should be obvious that various other adaptations and modifications can be envisioned by those persons skilled in such art without departing from either the spirit of the invention or the scope of the appended claims.

INDUSTRIAL USE

The invention has industrial use in the concrete production industry.

I claim:

1. A concrete mixing control apparatus comprising:

a concrete mixer with an interior surface;

at least one sensor to monitor one of pressure and stress attached to said interior surface of said concrete mixer;

a liquid supply tube attached to and in fluid communication with said concrete mixer;

a valve controlling the flow of a liquid through said liquid supply tube;

a liquid flow meter operatively connected to said liquid supply tube between said valve and said concrete mixer; and a computer processing unit operably connected to said at least one sensor and said liquid flow meter so as to calculate the slump within said concrete mixer, said computer processing unit receives and analyzes data from said at least one sensor to calculate rheological property values, records a first interval of time that said at least one sensor receives a load as said concrete mixer rotates and said sensor is submerged within a concrete mixture, records a second interval of time that said at least one sensor not loaded as said concrete mixer rotates and said at least one sensor emerges from the concrete mixture, calculates a volume of the concrete mixture within said concrete mixer by analyzing said first and second intervals; compares an output from said at least one sensor between a rotation of said concrete mixer and at least the immediately prior rotation of said concrete mixer until said output of force on said at least one sensor is generally consistent within a predetermined range of a predetermined force and calculates an amount of additional liquid to be added to the concrete mixture within the concrete mixer based on a desired slump inputted with an input device, and wherein said concrete mixing control apparatus is configured to add between approximately eighty-five (85) percent and approximately ninety-five (95) percent of said calculated amount of additional liquid to the concrete mixture.

2. A concrete mixing control apparatus according to claim 1 further comprising:

a data storage unit operably connected to said computer processing unit; and a display operably connected to said computer processing unit.

3. A concrete mixing control apparatus according to claim 2 wherein a plurality of sensors are attached to said interior surface of said concrete mixer.

4. A concrete mixing control apparatus according to claim 2 wherein said valve is operably connected to said computer processing unit and controlled by said computer processing unit.

5. A concrete mixing control apparatus according to claim 2 further having an input means operably connected to said computer processing unit to enter one or more of a requested slump, mix and customer information.

6. A concrete mixing control apparatus according to claim 5 wherein said input means is one of a touch screen, voice recognition, keyboard and alphanumeric keypad.

7. A concrete mixing control apparatus according to claim 5 wherein said input device permits the user override the data from said sensors and said computer processing unit.

8. A concrete mixing control apparatus according to claim 2 wherein said data storage unit is in a remote location from said concrete mixer.

9. A concrete mixing control apparatus according to claim 2 further including an output means.

10. A concrete mixing control apparatus according to claim 9 wherein said output means is a printer.

11. A concrete mixing control apparatus according to claim 2 wherein said computer processing unit, input means, data storage, display and an output means separately or in combination are in a remote location from said concrete mixer, wherein said sensors, valve and flow meter are operably connected by a transmitter and a receiver at said concrete mixer and at the remote location.

12. A concrete mixing control apparatus according to claim 2 further having a global positioning satellite receiving unit having a digital output operably connected to said data storage unit.

13. A concrete mixing control apparatus according to claim 2 further having a temperature sensor attached to said interior surface of said concrete mixer and operably connected to said data storage unit.

14. A concrete mixing control apparatus according to claim 2 further having a moisture sensor attached to said interior surface of said concrete mixer and operably connected to said data storage unit.

15. A concrete mixing control apparatus according to claim 2 further having a mixer pour valve operably connected to said computer processing unit.

16. A concrete mixing control apparatus according to claim 2 wherein said computer processing unit analyses said input from said sensor to determine a start and an end time of a pour of the concrete mixture.

* * * * *